United States Patent [19]
Itaya et al.

[11] Patent Number: 5,821,330
[45] Date of Patent: Oct. 13, 1998

[54] PEPTIDE HAVING INFLAMMATION AFFINITY AND RADIOACTIVE DIAGNOSTIC CONTAINING THE SAME

[75] Inventors: Yoshitoshi Itaya; Koichi Hanaoka, both of Sodegaura; Yoshifumi Shirakami, Ichihara, all of Japan

[73] Assignee: Nihon Medi-Physics Co., Ltd., Hyogo, Japan

[21] Appl. No.: 327,459

[22] Filed: Oct. 21, 1994

[30] Foreign Application Priority Data

Oct. 22, 1993 [JP] Japan ................................. 5-287752

[51] Int. Cl.⁶ .............................. C07K 5/00; A61K 38/04
[52] U.S. Cl. ..................... 530/326; 530/327; 530/328; 530/329; 530/345
[58] Field of Search ................................. 530/326, 327, 530/328, 329, 345

[56] References Cited

U.S. PATENT DOCUMENTS 4,926,869  5/1990  Rubin ........................................ 128/654

FOREIGN PATENT DOCUMENTS

| 0227110 | 7/1987 | European Pat. Off. ........ C12N 15/00 |
| 0584421 | 3/1994 | European Pat. Off. ........ C12N 15/13 |
| 63-502280 | 9/1988 | Japan . | |

OTHER PUBLICATIONS

Takashi Ohnishi et al., Nuclear Medicine (Kaku Igaku), vol. 26, pp. 1371–1379, 1989.

Frans H.M. Corstens et al., Seminars in Nuclear Medicine, vol. 13, No. 2, Apr., pp. 148–164, 1993.

Kazuo Ito, Nuclear Medicine (Kaku Igaku), vol. 24, pp. 341–351, 1987.

*Primary Examiner*—Avis M. Davenport
*Attorney, Agent, or Firm*—Darby & Darby

[57] ABSTRACT

A peptide having affinity with inflammation is disclosed, which contains at least one of the following amino acid sequences:

LLGGPS (SEQ ID NO:1),
LLGGPSV (SEQ ID NO:2),
KEYKAKVSNKALPAPIEKTISK (SEQ ID NO:3),
KEYKCKVSNKALPAPIEKTISK (SEQ ID NO:4),
KTKPREQQYNSTYR (SEQ ID NO:5), and
KTKPREQQYNSTYRVV (SEQ ID NO:6), wherein A, C, E, G, I, K, L, N, P, Q, R, S, T, V, and Y represent amino acid residues expressed by standard one-letter symbols. According to the present invention, a peptide and its chemically modified substances, radioactive metal labeled peptides derived therefrom, and radioactive diagnostics comprising such peptide are provided, which are useful for imaging inflammation region and easy in preparation handling, and accumulate at inflammation site immediately after administration while being excellent in clearance into urine. The imaging is possible in several ten minutes after administration.

19 Claims, 2 Drawing Sheets

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:1:

Leu   Leu   Gly   Gly   Pro   Ser
    1                          5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:2:

Leu   Leu   Gly   Gly   Pro   Ser   Val
    1                          5

( 2 ) INFORMATION FOR SEQ ID NO:3:

( i ) SEQUENCE CHARACTERISTICS:
        ( A ) LENGTH: 22 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:3:

Lys   Glu   Tyr   Lys   Ala   Lys   Val   Ser   Asn   Lys   Ala   Leu   Pro   Ala   Pro   Ile
    1                      5                      10                    15

Glu   Lys   Thr   Ile   Ser   Lys 2 0

(2) INFORMATION FOR SEQ ID NO:4:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: N-terminal (xi) SEQUENCE DESCRIPTION: SEQ ID NO:4:

```
Lys  Glu  Tyr  Lys  Cys  Lys  Val  Ser  Asn  Lys  Ala  Leu  Pro  Ala  Pro  Ile
1                   5                        10                       15
Glu  Lys  Thr  Ile  Ser  Lys
                20
```

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: N-terminal (xi) SEQUENCE DESCRIPTION: SEQ ID NO:5:

```
Lys  Thr  Lys  Pro  Arg  Glu  Gln  Gln  Tyr  Asn  Ser  Thr  Tyr  Arg
1                   5                        10
```

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: N-terminal (xi) SEQUENCE DESCRIPTION: SEQ ID NO:6:

```
Lys  Thr  Lys  Pro  Arg  Glu  Gln  Gln  Tyr  Asn  Ser  Thr  Tyr  Arg  Val  Val
1                   5                        10                       15
```

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: N-terminal ( i x ) FEATURE:
  ( A ) NAME/KEY: Modified-site
  ( B ) LOCATION: 1..2
  ( D ) OTHER INFORMATION: /note= "DTPA(X2) ADDED TO LYS"

( x i ) SEQUENCE DESCRIPTION: SEQ ID NO:7:

Lys Gly Gly Pro Glu Leu Leu Gly Gly Pro Ser Val
1               5                   10

( 2 ) INFORMATION FOR SEQ ID NO:8:

( i ) SEQUENCE CHARACTERISTICS:
  ( A ) LENGTH: 12 amino acids
  ( B ) TYPE: amino acid
  ( C ) STRANDEDNESS: Not Relevant
  ( D ) TOPOLOGY: Not Relevant ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:8:

Cys Gly Cys Gly Gly Leu Leu Gly Gly Pro Ser Val
1               5                   10

( 2 ) INFORMATION FOR SEQ ID NO:9:

( i ) SEQUENCE CHARACTERISTICS:
  ( A ) LENGTH: 33 amino acids
  ( B ) TYPE: amino acid
  ( C ) STRANDEDNESS: Not Relevant
  ( D ) TOPOLOGY: Not Relevant ( i i ) MOLECULE TYPE: peptide ( i i i ) HYPOTHETICAL: NO ( v ) FRAGMENT TYPE: N-terminal ( i x ) FEATURE:
  ( A ) NAME/KEY: Modified-site
  ( B ) LOCATION: 1..3
  ( D ) OTHER INFORMATION: /note= "Acm IS AN ACETAMIDE METHYL
   GROUP ADDED AT POSITIONS 1 AND 3."

( x i ) SEQUENCE DESCRIPTION: SEQ ID NO:9:

Cys Gly Cys Gly Gly Pro Glu Leu Leu Gly Gly Pro Ser Val Pro Glu
1               5                   10                  15

Leu Leu Gly Gly Pro Ser Val Pro Glu Leu Leu Gly Gly Pro Ser Val
            20                  25                  30

Ala ( 2 ) INFORMATION FOR SEQ ID NO:10:

( i ) SEQUENCE CHARACTERISTICS:
  ( A ) LENGTH: 6 amino acids
  ( B ) TYPE: amino acid
  ( C ) STRANDEDNESS: Not Relevant
  ( D ) TOPOLOGY: Not Relevant ( i i ) MOLECULE TYPE: peptide ( i i i ) HYPOTHETICAL: NO ( v ) FRAGMENT TYPE: N-terminal ( i x ) FEATURE:
  ( A ) NAME/KEY: Modified-site
  ( B ) LOCATION: 1..2
  ( D ) OTHER INFORMATION: /note= "(PELLGGPSV)4K2 ADDED AT

POSITION 1."

(x i) SEQUENCE DESCRIPTION: SEQ ID NO:10:

Lys Gly Gly Cys Gly Cys
1               5

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (i i) MOLECULE TYPE: peptide (i i i) HYPOTHETICAL: NO (v) FRAGMENT TYPE: N-terminal (i x) FEATURE:
        (A) NAME/KEY: Modified-site
        (B) LOCATION: 8..11
        (D) OTHER INFORMATION: /note= "SULFO SMCC
        (SULFOSUCCINIMIDYL
            4-(N- MALEIMIDEMETHYL)CYCLOHEXANE-1-CARBOXYLATE ADDED AT
            POSITION 8, x +y s 5."

(x i) SEQUENCE DESCRIPTION: SEQ ID NO:11:

Leu Leu Gly Gly Pro Ser Val Cys Cys His Ile
1               5                       10

(2) INFORMATION FOR SEQ ID NO:12:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (i i) MOLECULE TYPE: peptide (i i i) HYPOTHETICAL: NO (v) FRAGMENT TYPE: N-terminal (x i) SEQUENCE DESCRIPTION: SEQ ID NO:12:

Lys Gly Gly Pro Glu Leu Leu Gly Gly Pro Ser Val
1               5                       10

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: Not Relevant (i i) MOLECULE TYPE: peptide (i i i) HYPOTHETICAL: NO (v) FRAGMENT TYPE: N-terminal (x i) SEQUENCE DESCRIPTION: SEQ ID NO:13:

Leu Leu Gly Gly Pro Ser Val Cys
1               5

(2) INFORMATION FOR SEQ ID NO:14:

(i) SEQUENCE CHARACTERISTICS:
        (A) LENGTH: 28 amino acids ( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: N-terminal ( i x ) FEATURE:
( A ) NAME/KEY: Modified-site
( B ) LOCATION: 1..3
( D ) OTHER INFORMATION: /note= "ACETAMIDE METHYL GROUP
ADDED AT POSITION 1 AND 3."

( x i ) SEQUENCE DESCRIPTION: SEQ ID NO:14:

```
Cys Gly Cys Gly Gly Gly Lys Glu Tyr Lys Ala Lys Val Ser Asn Lys
 1               5                  10                  15
Ala Leu Pro Ala Pro Ile Glu Lys Thr Ile Ser Lys
            20                  25
```

( 2 ) INFORMATION FOR SEQ ID NO:15:

( i ) SEQUENCE CHARACTERISTICS:
( A ) LENGTH: 21 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: N-terminal ( i x ) FEATURE:
( A ) NAME/KEY: Modified-site
( B ) LOCATION: 1..3
( D ) OTHER INFORMATION: /note= "ACETAMIDE METHYL GROUP
ADDED AT POSITIONS 1 AND 3."

( x i ) SEQUENCE DESCRIPTION: SEQ ID NO:15:

```
Cys Gly Cys Gly Gly Lys Thr Lys Pro Arg Glu Gln Gln Tyr Asn Ser
 1               5                  10                  15
Thr Tyr Arg Val Val
            20
```

( 2 ) INFORMATION FOR SEQ ID NO:16:

( i ) SEQUENCE CHARACTERISTICS:
( A ) LENGTH: 44 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: N-terminal ( i x ) FEATURE:
( A ) NAME/KEY: Modified-site
( B ) LOCATION: 42..44
( D ) OTHER INFORMATION: /note= "ACETAMIDE METHYL GROUP
ADDED AT POSITIONS 42 AND 44."

( x i ) SEQUENCE DESCRIPTION: SEQ ID NO:16:

```
Pro Glu Leu Leu Gly Gly Pro Ser Val Pro Glu Leu Leu Gly Gly Pro
 1               5                  10                  15
Ser Val Pro Glu Leu Leu Gly Gly Pro Ser Val Pro Glu Leu Leu Gly
```

```
                    20                      25                       30
    Gly Pro Ser Val Lys Lys Lys Gly Gly Cys Gly Cys
                35                      40
```

(2) INFORMATION FOR SEQ ID NO:17:

(i) SEQUENCE CHARACTERISTICS:
  (A) LENGTH: 33 amino acids
  (B) TYPE: amino acid
  (C) STRANDEDNESS: Not Relevant
  (D) TOPOLOGY: Not Relevant (ii) MOLECULE TYPE: peptide (iii) HYPOTHETICAL: NO (v) FRAGMENT TYPE: N-terminal (ix) FEATURE:
  (A) NAME/KEY: Modified-site
  (B) LOCATION: 1..3
  (D) OTHER INFORMATION: /note= "ACETAMIDE METHYL GROUP ADDED AT POSTIONS 1 AND 3."

(xi) SEQUENCE DESCRIPTION: SEQ ID NO:17:

```
    Cys Gly Cys Gly Gly Pro Glu Leu Leu Gly Gly Pro Ser Val Pro Glu
    1               5                   10                  15
    Leu Leu Gly Gly Pro Ser Val Pro Glu Leu Leu Gly Gly Pro Ser Val
                20                  25                  30
    Ala
```

PEPTIDE HAVING INFLAMMATION AFFINITY AND RADIOACTIVE DIAGNOSTIC CONTAINING THE SAME

The present invention relates to a peptide having affinity with inflammatory cells and its derivatives or chemically modified substances. The present invention also relates to a radioactive diagnostic useful for diagnosing inflammation sites in living body of mammals including human, which comprises the above peptide and a radioactive metal label for the peptide.

The term "inflammation" covers so-called inflammatory responses wholly, including those caused by infectious diseases or on the periphery of tumors. Inflammation is induced by physical or chemical reactions due to heat, radiant energy, chemical substances, mechanical trauma or the like, and is also noted on infectious diseases caused by invasion into living bodies of foreign substances such as virus and bacteria, or on the periphery of tumors resulting from, for example, mutation of DNA. Inflammation is a series of reactions initiated by reaction of tissue cells subjected to inflammatory stimuli and by subsequent reactions in microcirculation system, particularly with protein permeation through blood vessels, followed by exudation and infiltration of leukocytes and granuloma formation to healing; it may be regarded as a biological defense reaction of the host for preventing foreign substance from invading into the living body or for normalizing inflammation sites.

Known radioactive diagnostic agents for imaging inflammations in living body including those caused by infectious diseases or on the periphery of tumors include gallium-67 citrate (Takashi Onishi, Nuclear Medicine (Kaku Igaku), Vol. 26, pp 1371–9, 1989), radioactive metal labeled polyclonal antibodies (JP-A-63502280 of Rabin. R. H et al, and Frans. H. M et al, Seminars in Nuclear Medicine, Vol 13, No. 2, April, pp 148–164, 1993), and radiolabeled leukocytes (Kazuo Ito, Nuclear Medicine (Kaku Igaku), Vol. 24, pp 341–51, 1987).

Gallium-67 citrate contains gallium-67 which has a long half-life of 3.26 days, and the radioactive metal labeled polyclonal antibodies per se are also long in half-life in blood; thus both agents make the radioactive metal stay in the body for a long period of time giving unnecessary exposure to the patient. Furthermore, imaging takes 20 hours or longer with both agents. Thus, it has been impossible to get diagnostic information quickly for patients in immediate need of treatment.

Radiolabeled leukocyte diagnostic has been used in clinical practice as highly advanced medical care. However, this diagnostic requires a complicated procedure with advanced skill in which the surgeon has to prepare it by collecting blood from the patient, separating and refining leukocytes therefrom, labeling them with a radioactive metal such as indium-111 and again refining them prior to administration. This diagnostic is not prevalent because it requires a sterile room and other special equipment for preparation and thus is only usable in limited facilities. In addition, the diagnostic may be hazardous to the surgeon for infection if the patient is infected by viral hepatitis, HIV or the like.

In view of the above-mentioned disadvantages of conventional compounds and their radiolabelled products such as the unnecessary exposure to patients, limitation of facilities for preparation, difficulty to get image information quickly, complicated handling in preparation, and risk of infection to the operator, it is an object of the present invention to provide peptides and their chemically modified substances, radioactive metal labeled peptides derived therefrom, and radioactive diagnostics comprising such peptides, which are useful for imaging inflammation sites in living body of mammals including human, easy in preparation handling, and capable of accumulating at inflammation site quickly after administration and staying there for a suitable time for imaging while being excellent in clearance into urine.

As the result of the intensive researches made by the present inventors to attain the object, peptides at least a part of which comprises a specific amino acid sequence have been found to be useful and have led to accomplishment of the present inventions. One aspect of the present invention is directed to peptides having affinity with inflammation, which contain at least one amino acid sequence selected from the group consisting of LLGGPS (SEQ ID NO:1),
LLGGPSV (SEQ ID NO:2),
KEYKAKVSNKALPAPIEKTISK (SEQ ID NO:3),
KEYKCKVSNKALPAPIEKTISK (SEQ ID NO:4),
KTKPREQQYNSTYR (SEQ ID NO:5), and
KTKPREQQYNSTYRVV (SEQ ID NO:6), where A, C, E, G, I, K, L, N, P, Q, R, S, T, V, and Y represent amino acid residues expressed by standard one-letter symbols. These specific amino acid sequences hereinafter referred to as "basic amino acid sequences". Another aspect of the present invention is directed to derivatives of the above-mentioned peptides, the peptides and the derivatives labeled with radioactive metals, and radioactive diagnostics containing the peptides and/or the derivatives. Amino acid residues are expressed hereinafter by standard one- or three-letter symbols.

The peptides according to the present invention may be prepared by Fmoc method, a solid phase synthetic method, using a peptide synthesizer manufactured by Applied Biosystem. The target peptide may be obtained by simultaneous deprotection and separation from resinous carrier, of the completed peptide bonded to the solid layer, followed by purification with high-performance liquid chromatography (hereinafter referred to as "HPLC") utilizing a reverse phase column. The peptide may be synthesized in liquid phase or may be collected from animals or the like.

The derivatives of peptide having affinity with inflammation are those that are denatured or chemically modified so as to increase capability of accumulating at inflammatory cells, as explained hereunder. Examples of such derivatives include those in which peptides containing basic amino acid sequences are combined in parallel by use of Fmoc-K (Fmoc), those in which several peptides containing basic amino acid sequences are combined in tandem, those in which peptides containing basic amino acid sequences are combined with a bifunctional cross linking agent, those in which peptides containing basic amino acid sequences are combined with a bifunctional cross linking agent and further be combined with a carrier such as polylysine or chitosan, those in which peptides are chemically modified by, for example, acetylation or amidation at N-terminal and/or C-terminal, and those in which peptides are substituted with amino acids of D-configuration in part or as a whole.

The above-mentioned bifunctional cross linking agent is useful for increasing peptide efficacy by combining a plurality of peptides having affinity with inflammation according to the present invention to increase peptide concentration or by combining with carriers to increase the amount of peptides to be held by the carrier. Preferably, the bifunctional cross linking agent is one capable of selectively bonding to amino acid residues, including sulfosuccinimidyl 4-(N- maleimidemethyl)cyclohexane-1-carboxylate (hereinafter abbreviated as "Sulfo-SMCC"), 3-maleimidebenzoic acid N-hydroxysuccinimide ester (hereinafter abbreviated as "MBS"), N-(ε-maleimidecaproyloxy)succinimide (hereinafter abbreviated as "EMCS"), and succinimydyl 4-(p-maleimidephenyl)butylate (hereinafter abbreviated as "SMPB"). Particularly preferable one is Sulfo-SMCC.

Preferable examples of the carrier that can combine a plurality of the peptides having affinity with inflammation include polylysine and chitosan. Chitosan is particularly preferable.

A diagnostic useful for imaging inflammation can be obtained by labeling the present peptide having affinity with inflammation or its derivatives with radioactive metal ion such as technetium-99m ($^{99m}$Tc) and indium-111 ($^{111}$In). A bifunctional ligand is conveniently used for labeling with radioactive metal ion. Preferable examples of the ligand include diethylenetriamine pentaacetic acid (hereinafter abbreviated as "DTPA"), ethylenediaminetetraacetic acid (hereinafter abbreviated as "EDTA"), and 1,4,7,10-tetraazacyclododecane-1-aminoethylcarbamoylmethyl-4,7, 10-tris[(R,S)-methylacetic acid] (hereinafter abbreviated as "DO3MA"). DTPA is most preferable.

Alternatively, labeling with a radioactive metal may be carried out by dissolving the present peptide or a derivative thereof in a physiological saline, an aqueous buffer solution or the like and allowing it to react with a radioactive metal. In case of technetium-99m, a peptide can be labeled by an ordinary process wherein a reduction agent having a proper redox potential such as stannous chloride is added to the peptide, followed by mixing with a sodium pertechnetate solution. In case of indium-111, a peptide can be labeled by mixing the peptide with a weak acidic aqueous solution containing indium-111 ions. If required, unreacted pertechnetate ions or indium-111 ions may be removed by HPLC or other means.

Furthermore, the present diagnostic may be provided in a form of a kit so that it can be prepared as required. The kit may include a pharmaceutically acceptable stabilizer such as ascorbic acid or p-aminobenzoic acid, a pH adjusting agent such as an aqueous buffer solution, an excipient such as D-mannitol, and an agent useful for improving radiochemical purity such as tartaric acid, or malonic acid.

Pharmaceutically acceptable peptide compounds comprising a peptide containing a radioactive metal in accordance with the present invention efficiently accumulate at inflammation sites just after generally-employed parenteral administration such as intravenous bolus injection, attain quick distribution of the radioactive substance, provide a target site/background ratio sufficient to complete imaging within one hour after administration, and stay at the target site for a suitable period of time for imaging and thereafter are quickly excreted into urine via kidney; all of these features are desirable for a diagnostic. Thus, the peptide has excellent characteristics for overcoming conventional problems while enabling a diagnosis to be made by use of a radioactive imaging apparatus that is generally available.

The present radioactive diagnostic comprising the peptide having affinity with inflammation can be administered parenterally in accordance with a common practice such as intravenous bolus injection; the amount of administration is decided so as to obtain a radiation dose sufficient for imaging in consideration of various conditions such as weight and age of the patient as well as type of radioactive imaging apparatus. In case of human, a radiation dose from 185 to 1110 MBq is usually preferable.

Now, examples of the peptide having affinity with inflammation and its derivative according to the present invention are shown hereunder.

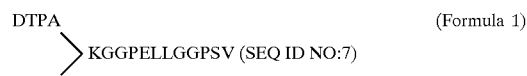

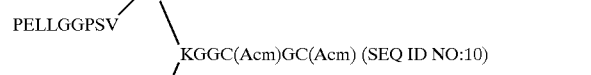

BRIEF DESCRIPTION OF DRAWINGS

Now, the present invention is illustrated in more details by way of examples and the drawings.

Figure 1:
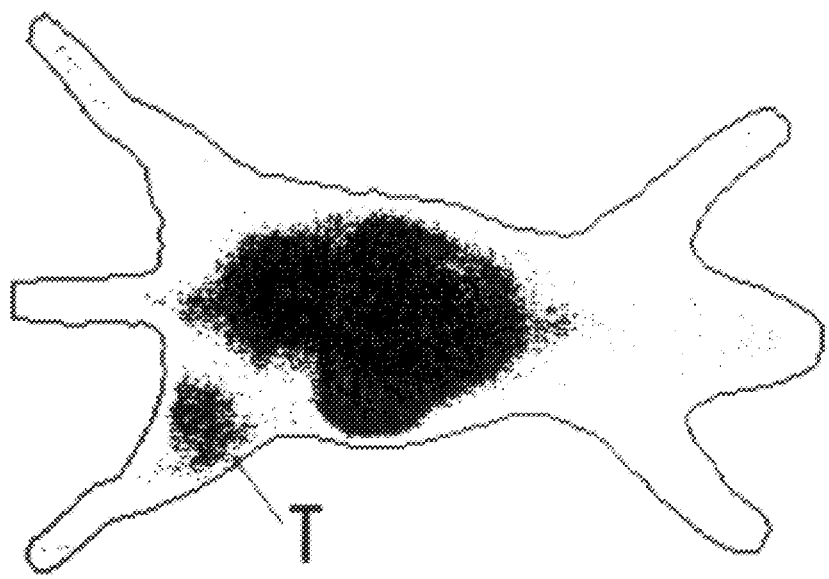
FIG. 1 is a whole body scintigram of an inflammation model rat one hour after administration of radioactive metal labeled Peptide-4.
Figure 2:
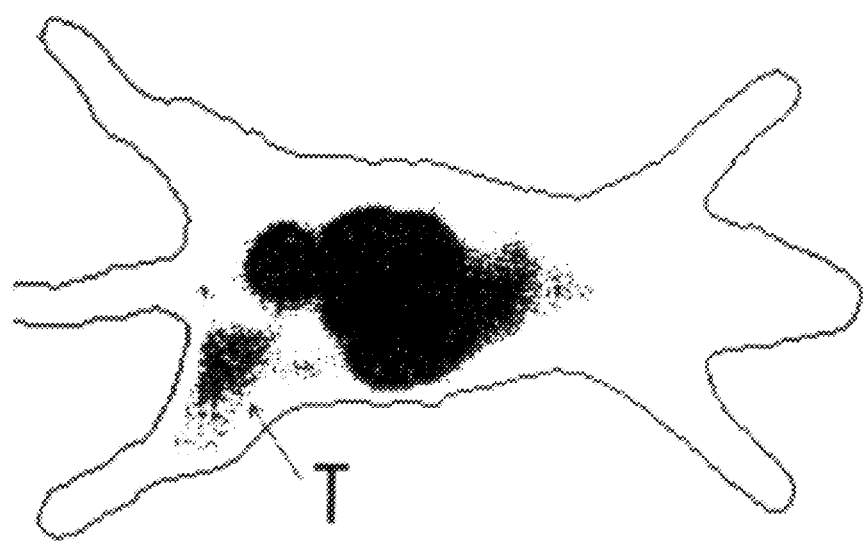
FIG. 2 is a whole body scintigram of an inflammation model rat one hour after administration of radioactive metal labeled Peptide-5.
Figure 3:
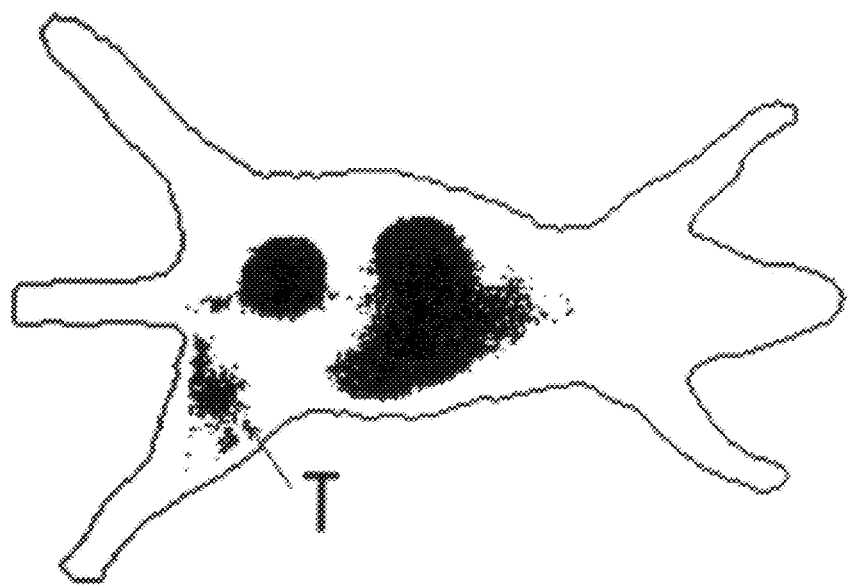
FIG. 3 is a whole body scintigram of an inflammation model rat one hour after administration of radioactive metal labeled Peptide-6.
Figure 4:
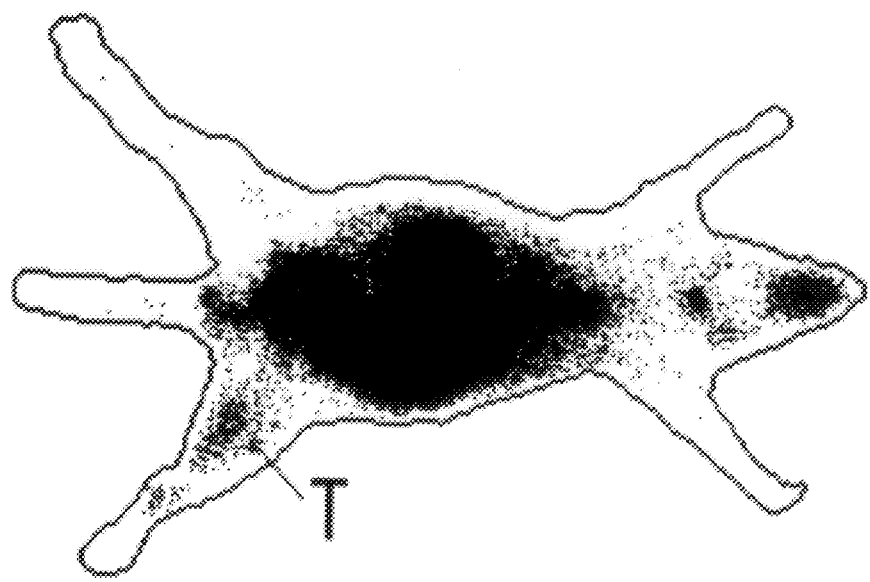
FIG. 4 is a whole body scintigram of a model rat with infectious disease one hour after administration of radioactive metal labeled Peptide-6.

While the technetium-99m labeling was made in the examples according to the process described in WO-A-92/13572, the object of the example is to prove that the peptide according to the present invention is able to image inflammation sites without change in performance regardless of kinds of nuclide or labeling method.

EXAMPLE 1

Synthesis of KGGPELLGGPSV (SEQ ID NO:12) (Peptide-1)

Synthesis was made with Peptide Synthesizer (Model 431A) manufactured by Applied Biosystems using HMP Resin by Fmoc process under 0.25 mM scale condition. Excision of the peptide was made by a reaction for 2.5 hours in aqueous 95% trifluoroacetic acid (hereinafter abbreviated as "TFA") containing 2.5% ethanedithiol (hereinafter abbreviated as "EDT"). Purification was made by HPLC under the following conditions:

Column: YMC-PackR&D-ODS-5-ST (4.6×150 mm)
Elution velocity: 6 mL/min
Eluent A: 0.1% TFA/purified water
Eluent B: 0.1% TFA/acetonitrile
Concentration gradient: 0 min (10% B)→15 min (20% B)→40 min (50% B)

Then, PICO•TAG-TM-Workstation manufactured by Waters was used for identifying the amino acid composition corresponding to the main peak. After it was confirmed that the composition was of the target peptide, the peak coinciding with the amino acid composition was freeze-dried to yield 59.6 mg of the lyophilized product. The analytical value (number per molecule) for the amino acid composition of the product peptide is shown below together with the theoretical value in parentheses:

Glu:1.0 (1), Ser:1.3 (1), Gly:4.4 (4), Pro:2.0 (2),
Val:1.1 (1), Leu:2.1 (2), Lys:1.2 (1).

For the purpose of confirming the reliability of the Peptide Synthesizer, the amino acid sequence of the product peptide was determined by Protein Sequencer (a peptide automatic analyzer) Model 477A manufactured by Applied Biosystems. In addition, C-terminal analysis was made for confirming the C-terminal. As a result, the sequence from the N-terminal to S at the eleventh position coincided with the target sequence. The C-terminal analysis showed that the C-terminal was V. Thus, the peptide was confirmed to have an amino acid sequence of KGGPELLGGPSV (SEQ ID NO:12)

EXAMPLE 2

Synthesis of CGCGGLLGGPSV (SEQ ID NO:8) (Peptide-2)

Synthesis was made by the method described in EXAMPLE 1. Purification was made by UPLC under the following conditions:

Column: YMC-PackR&D-ODS-5-ST (4.6×150 mm)
Elution velocity; 1 mL/min
Eluent A: 0.1% TFA/purified water
Eluent B: 0.1% TFA/acetonitrile
Concentration gradient: 0 min (5% B)→40 min (30% B)→120 min (60% B)

After the amino acid composition corresponding to the main peak is determined in the same way as EXAMPLE 1 to confirm that the target peptide was obtained, the peak obtained was freeze-dried to yield 20 mg of the lyophilized product. The analytical value (number per molecule) for the amino acid composition of the product peptide is shown below together with the theoretical value in parentheses:

Ser:1.0 (1), Gly:4.9 (5), Pro:1.0 (1), Val:1.0 (1),
Cys:0.9 (2), Leu:2.0 (2).

EXAMPLE 3

Synthesis of LLGGPSVC (SEQ ID NO:13) (Peptide-3)

A peptide having LLGGPSVC (SEQ ID NO:13) amino acid sequence was synthesized in an amount of 25 mg according to the method described in EXAMPLE 1, and the peptide was analyzed for the amino acid composition. The analytical value (number per molecule) for the amino acid composition of the product peptide is shown below together with the theoretical value in parentheses:

Ser:0.9 (1), Gly:2.0 (2), Val:10 (1), Leu:1.8 (2),
Pro:1.0 (1), Cys:1.2 (1).

EXAMPLE 4

Synthesis of C(Acm) GC(Acm) GGGKEYKAKVSNKALPAPIEKTISK (SEQ ID NO:14) (Peptide-4)

Synthesis was made by the method described in EXAMPLE 1. Acm (acetamide methyl group) is a protective group for —SH group in cysteine. Excision of the peptide was made by allowing 100 mg of the resultant compound to react for 2.5 hours in 10 ml of aqueous solution in which 0.25 ml of EDT 0.75 g of crystalline phenol, 0.5 ml of thioanisole, 0.5 ml of purified water and 9.5 ml of TFA were axed. Purification was made by HPLC under the following conditions:

Column: Y–C-PackR&D-ODS-5-ST (20×150 mm)
Elution velocity: 8 mL/min
Eluent A: 0.1% TFA/purified water
Eluent B: 0.1% TFA/acetonitrile
Concentration gradient: 0 min (10% B)→15 min (15% B)→40 min (50% B)

After the amino acid composition corresponding to the main peak is determined in the same way as EXAMPLE 1 to confirm that the target peptide was obtained, the peak coinciding with the amino acid composition was freeze-dried to yield 45 mg of the lyophilized product with purity of 95% or more. Since C(Acm) is unable to be identified by PICO•TAG method, the presence of C(Acm)GC(Acm) was confirmed by technetium-99m labeling. The analytical value (number per molecule) for the amino acid composition of the product peptide is shown below together with the theoretical value in parentheses:

Asn:1.1 (1), Glu:2.0 (2), Ser:2.3 (2), Gly:4.4 (4), Thr:1.0 (1),
Ala:3.2 (3), Pro:2.1 (2), Tyr:0.6 (1), Val:0.9 (1), Ile:2.8 (2),
Leu:1.3 (1), Lys:5.7 (6), Cys:–(2).

The amino acid sequence of the resulting peptide was determined using the same Sequencer as EXAMPLE 1; the sequence from the N-terminal to the 26th residues coincided with the target sequence. Thus, the peptide was confirmed to have an amino acid sequence of C(Acm)GC(Acm) GGGKEYKAKVSNKALPAPIEKTISK(SEQ ID NO:14).

EXAMPLE 5

Synthesis of C(Acm)GC(Acm) GGKTKPREQQYNSTYRVV (SEQ ID NO:15) (Peptide-5)

Synthesis was made by the method described in EXAMPLE 1. Excision of the peptide was made by allowing 150 mg of the resultant compound to react for 1.5 hours in 10 ml of aqueous solution in which 0.25 ml of EDT, 0.75 g of crystalline phenol, 0.5 ml of thioanisole, 0.5 ml of purified water and 9.5 ml of TFA were mixed. Purification was made by HPLC under the following conditions;

Column: YMC-PackR&D-ODS-5-ST (20×150 mm)
Elution velocity: 8 mL/min
Eluent A: 0.1% TFA/purified water
Eluent B: 0.1% TFA/acetonitrile
Concentration gradient: 0 min (10% B)→15 min (10% B)→90 min (40% B)

Then, using the same analysis unit as EXAMPLE 1, the amino acid composition corresponding to the main peak was identified. After it was confirmed that the composition was of the target peptide, the peak coinciding with the amino acid composition was freeze-dried to yield 51 mg of the lyophilized product of which purity was not less than 95%. The analytical value (number per molecule) for the amino acid composition of the product peptide is shown below together with the theoretical value in parentheses:

Asp:1.1 (1), Glx:3.1 (3) Ser:1.0 (1) Gly:3.3 (3), Arg:2.1 (2), Thr:2.2 (2), Pro:1.1 (1), Tyr:1.2 (2), Val:1.7 (2), Cys:–(2), Lys:5.9 (6)

EXAMPLE 6

Synthesis of (PELLGGPSV)×4 in parallel (K)×2 in parallel (KGGC(Acm)GC(Acm)) (SEQ ID NO: 16) (Peptide-6)

Synthesis was made by the method described in EXAMPLE 1. Purification was made by HPLC under the following conditions:

Column: YMC-PackR&D-ODS-5-ST (20×150 mm)

Elution velocity: 8 mL/min

Eluent A: 0.1% TFA/purified water

Eluent B: 0.1% TFA/acetonitrile

Concentration gradient: 0 min (15% B)→15 min (15% B)→100 min (60% B)

Then, using the same analysis unit as EXAMPLE 1, the amino acid composition corresponding to the main peak was identified. After it was confirmed that the composition was of the target peptide, the peak coinciding with the amino acid composition was freeze-dried to yield 22.1 mg of the lyophilized product. The analytical value (number per molecule) for the amino acid composition of the product peptide is shown below together with the theoretical value in parentheses:

Glu:3.9 (4), Ser:4.1 (4), Gly:11.8 (11), Pro:7.9 (8), Val:2.9 (4), Leu:7.6 (8), Lys:2.1 (3), Cys:–(2)

EXAMPLE 7

Synthesis of C(Acm)GC(Acm)GG[(PELLGGPSV)× 3 repeats in tandem]A (SEQ ID NO:17) (Peptide-7)

Synthesis was made by the method described in EXAMPLE 1. Purification was made by HPLC under the following conditions:

Column: YMC-PackR&D-ODS-5-ST (20×150 mm)

Elution velocity: 8 mL/min

Eluent A: 0.1% TFA/purified water

Eluent B: 0.1% TFA/acetonitrile

Concentration gradient: 0 min (15% B)→15 min (15% B)→100 min (60% B)

Then, using the same analysis unit as EXAMPLE 1, the amino acid composition corresponding to the main peak was identified. After it was confirmed that the composition was of the target peptide, the peak coinciding with the amino acid composition was freeze-dried to yield 55.6 mg of the lyophilized product. The analytical value (number per molecule) for the amino acid composition of the product peptide is shown below together with the theoretical value in parentheses:

Glu:3.1 (3), Ser:3.0 (3), Gly:9.7 (9), Pro:6.9 (2), Val:2.9 (3), Leu:6.0 (6), Ala:2.0 (1)

EXAMPLE 8

Introduction of Bifunctional Ligand (DTPA) into Lysine Residue of Peptide-1

Peptide-1 obtained in EXAMPLE 1, in an amount of 5.0 µmol, was dissolved in 3.0 ml of a 0.1M phosphate buffer solution (pH 8.0); 10 times volume of DTPA anhydride was added to the mixture with agitation at room temperature and allowed to react for 30 minutes. Three peaks were obtained from the mixture by HPLC separation using 230 nm detection wavelength. Indium-111 was labeled to each of the peak components for determining the target peak; the labeling ratio was determined by electrophoresis using acethylcellulose membrane.

Radiochemical purity was 96.0% for peak 1, 98.0% for peak 2, and 38.0% for peak 3. The high labeling ratio of 98.0% for the peak 2 component led to the conclusion that this component was the target compound having the bifunctional ligand combined to the peptide. The peak 2 component was freeze-dried to yield 7.1 mg of the DTPA combined peptide.

EXAMPLE 9

Introduction of Bifunctional Ligand (DTPA) into Chitosan-Pentamer (CHI-Pentamer)

Chitosan-pentamer, in an amount of 32.8 µmol, was dissolved in 3.0 ml of a 0.1M bicarbonate buffer solution (pH 9.7); 5 times volume of DTPA anhydride was added to the mixture with agitation at room temperature and allowed to react for 1 hour. The mixture solution was refined by electrodialysis for 2.5 hours using the unit (Micro Acilyzer S1) of Asahi chemical Industry Co., Ltd. The resultant sample was analyzed quantitatively by ninhydrine reaction of the unreacted primary amines. The analysis showed the presence of at least two unreacted primary amines, indicating from 1 to 3 DTPAs were introduced into the CHI-pentamer.

EXAMPLE 10

Synthesis of Peptide-3-Sulfo-SMCC-CHI-pentamer-DTPA

DTPA-CHI-pentamer obtained in EXAMPLE 9, in an amount of 10 nmol, was dissolved in 8.0 ml of a 50 mM borate buffer solution (pH 7.6); 50 nmol of Sulfo-SMCC was added to the aqueous solution with agitation at 30° C. and the mixture was allowed to react for 1 hour. Purification was made by electrodialysis using the unit of Asahi Chemical Industry Co., Ltd. followed by dry-freezing. A 37.5% portion of the product compound was aliquoted and dissolved into a 0.1M tris-HCl buffer solution (pH 7.0). To this mixture, 12 µmol of Peptide-3 obtained in EXAMPLE 3 was added; the whole was allowed to react in a low temperature room overnight, then concentrated and purified by HPLC. Two peaks were obtained using 215 nm detection wavelength (retention time: 61 minutes for peak 1, and 73 minutes for peak 2). Indium-111 was labeled to each of the peak components, and radiochemical purity was determined by electrophoresis; peak 1 was 82.6% and peak 2 was 83.4%. Since hydrophobicity of the whole compound increases as the number of the peptides combined to CHI increases, further experiments were made using the peak 2 that appeared to be the target compound because of the longer HPLC retention time.

EXAMPLE 11

N-Terminal Acetylation of KGGPELLGGPSV (SEQ ID NO:12) (Peptide-1)

An amount of 8.0 µmol of Peptide-1 prepared in EXAMPLE 1 was dissolved in 1.0 mL of a 0.3M phosphate buffer solution (pH 7.3); 20 µl of acetic anhydride was added thereto with agitation at 4° C. and the mixture was allowed to react for 12 hours. After the completion of reaction, the N-terminal acetylation was checked by measuring absorbance at a wavelength of 570 nm. Result was 1.734 for N-terminal amine and 0.249 for N-terminal acetylated, which means that 85.7% was acetylated. It is known that as combination of acetyl group to N-terminal increases, the hydrophobicity of the peptide and retention time are extended upon reverse-phase HPLC. On this basis, the HPLC analysis was conducted and indicated that the retention time was 13.72 minutes for the starting peptide-1, and 14.93 minutes for the N-terminal acetylated peptide-1. The extension of about one minute of the retention time verified the acetylation of the N-terminal of the peptide.

EXAMPLE 12

C-Terminal Amidation and N-Terminal Acetylation of C(ACM)GC(Acm) GGGKEYKAKVSNKALPAPIEKTISK (SEQ ID NO:14) (Peptide-4)

In the process described in EXAMPLE 1, PAL (Peptide Amide Linker) Resin made by MILLIPORE was used in place of the HMP Resin to synthesize C(Acm)GC(Acm) GGGKEYKAKVSNKALPAPIEKTISK (SEQ ID NO:14) of which C-terminal was amidated. Then, its N-terminal was acetylated by acetic anhydride using N-hydroxybenzotriazole (HOBt) as an activation agent.

Excision of the peptide was made by allowing 150 mg of the resultant compound to react for 2 hours in 10 ml of aqueous solution in which 0.25 ml of EDT, 0.75 g of crystalline phenol, 0.5 ml of thioanisole, 0.5 ml of purified water and 9.5 ml of TFA were mixed. Purification was made by HPLC under the following conditions:

Column: YMC-PackR&D-ODS-5-ST (20×150 mm)

Elution velocity: 8 mL/min

Eluent A: 0.1% TFA/purified water

Eluent B: 0.1% TFA/acetonitrile

Concentration gradient: 0 min (10% B)→15 min (15% B)→75 min (50% B)

Then, using the same analysis unit as EXAMPLE 1 for analyzing the amino acid composition, the amino acid composition corresponding to the resultant main peak was identified. After it was confirmed that the composition was of the target peptide, the peak coinciding with the amino acid composition was freeze-dried to yield 32 mg of the lyophilized product of which purity was not less than 95%. The analytical value (number per molecule) for the amino acid composition of the product peptide is shown below together with the theoretical value in parentheses:

Asn:1.1 (1), Glu:2.1 (2), Ser:2.0 (2), Gly:3.8 (4), Thr:1.1 (1), Ala:3.1 (3), Pro:2.1 (2), Tyr:0.6 (1), Val:1.0 (1), Cys:–(2), Ile:2.2 (2), Leu:1.2 (1), Lys:5.9 (6)

EXAMPLE 13

C-Terminal Amidation and N-Terminal Acetylation of C(Acm)GC(Acm)GGKTKPREQQYNSTYRVV (SEQ ID NO:15) (Peptide-5)

In the process described in EXAMPLE 1, PAL Resin manufactured by MILLIPORE was used in place of the HMP Resin to synthesize C(Acm)GC(Acm) GGKTKPREQQYNSTYRVV (SEQ ID NO:15) of which C-terminal was amidated. Then, its N-terminal was acetylated by acetic anhydride using N-hydroxybenzotriazole (HOBt) as an activation agent.

Excision of the peptide was made by allowing 150 mg of the resultant compound to react for 1.5 hours in 10 ml of aqueous solution in which 0.25 ml of EDT, 0.75 g of crystalline phenol, 0.5 ml of thioanisole, 0.5 ml of purified water and 9.5 ml of TFA were mixed. Purification was made by HPLC under the following conditions:

Column: YMC-PackR&D-ODS-5- ST (20×150 mm)

Elution velocity: 8 mL/min

Eluent A: 0.1% TFA/purified water

Eluent B: 0.1% TFA/acetonitrile

Concentration gradient: 0 min (10% B)→15 min (10% B)→75 min (50% B)

Then, using the same analysis unit as EXAMPLE 1 for analyzing the amino acid composition, the amino acid composition corresponding to the resultant main peak was identified. After it was confirmed that the composition was the target peptide, the peak coinciding with the amino acid composition was freeze-dried to yield 23 mg of the lyophilized product of which purity is not less than 95%. The analytical value (number per molecule) for the amino acid composition of the product peptide is shown below together with the theoretical value in parentheses:

Asp:1.1 (1), Glx:3.2 (3), Ser:0.9 (1), Gly:3.1 (3), Arg:2.2 (2), Thr:2.2 (2), Pro:1.1 (1), Tyr:1.3 (2), Val:1.6 (2), Cys:–(2), Lys:5.9 (6)

EXAMPLE 14

Preparation of Indium-111 Labeled Peptide

Peptide-1-DTPA obtained in EXAMPLE 8, in an amount of 100 through 200 nmol was adjusted to pH 5.7 in a 0.1M citrate buffer solution, and then 37 to 74 MBq of indium ($^{111}$In) chloride was added thereto. After agitation, the solution was left as such for 15 minutes. A part of the solution was taken and checked for the labeling percentage by electrophoresis. The radiochemical purity of the target compound was 98%. Peptide-3-Sulfo-SMCC-CHI-DTPA obtained in EXAMPLE 10 was also labeled with In-111 in the same way as above, and the radiochemical purity of the target compound was 90%.

EXAMPLE 15

Technetium-99m Labeling of Peptides Containing CGC Sequence

An amount of 240–300 nmol of Peptide-2 obtained in EXAMPLE 2 was taken into each vial, and a volume of a 0.1M phosphate buffer solution (pH 8.0) was added thereto to adjust the whole molarity to 300 μmol Atmosphere in the vial was replaced with argon; then 180–300 nmol of dithiothreitol was added thereto, The mixture was then allowed to react for one hour at room temperature. Next, 120 nmol of stannous chloride and 740–1110 MBq of sodium pertechnetate were added. The mixture was left for one hour under gentle agitation. Peptide-2 labeled with technetium-99m was yielded. Peptide labeled had radiochemical purity not less than 90%.

EXAMPLE 16

Preparation of Glucoheptanate Labeled with Technetium-99m

An amount of 20.4 μmol of glucoheptanic acid was dissolved into a 0.1M phosphate buffer solution (pH 8.0) to adjust the total volume to 450 μl. Atmosphere in the vial was replaced with argon; then 120 μmol of stannous chloride and 1.5–2.2 GBq of sodium pertechnetate were added. The mixture was gently agitated for 30 minutes. Thereby, glucoheptanate labeled with technetium-99m was yielded.

EXAMPLE 17

Technetium-99m Labeling of Peptides Containing C(ACM)GC(Acm) Sequence

Experiments were made for all the peptides those prepared in EXAMPLEs 4, 5, 6 and 7. Each of the peptides was taken, in an amount of 0.2–1.0 μmol, into a vial respectively, and a volume of a 0.1M phosphate buffer solution (pH 8.0) was added thereto to adjust the whole volume to 500 μl. Atmosphere in the respective vial was replaced with argon. To each vial, 500 μl of 1.5–2.2 GBq/ml glucoheptanate labeled with technetium-99m yielded in EXAMPLE 16 was added and quickly agitated. Thereafter, the mixture was allowed to react for 20 minutes in a boiling water bath. Labeling percentage of all the experimented peptides after cooling was 90–95% according to TLC.

EXAMPLE 18

Imaging of Inflammation Sites Using Indium-111 Labeled Peptide

To the right femoral part of Sparague-Davley Rats weighing about 220 g, 100 μl of turpentine oil was subcutaneously administered. After 24 hours, when inflammation was clearly observed, Ravonal anesthesia was applied; then, Peptide-1-DTPA-indium-111 and Peptide-3-Sulfo-SMCC-CHI-DTPA-indium-111 obtained in EXAMPLE 14 were respectively administered in an amount of 3.7 MBq–7.4 MBq to the respective tail vein. Images were obtained with gamma camera one, three, and six hours later. A site of interest was set on the image, where the ratio ([T]/[B] ratio) of total counts for the inflammation site [T] to total counts for the corresponding normal site of the opposite leg [B] was determined. The [T]/[B] ratio, one hour after the administration, was 2.63 for Peptide-1-DTPA-indium-111 and 2.09 for Peptide-3-DTPA-indium-111, whereby the focal site was evidently imaged. Table 1 shows time course of the [T]/[B] ratios (mean value±standard error) for three rats with respective peptides.

TABLE 1

[T]/[B] ratio of In-111 labeled peptides in inflammation model rats

| Labeled Peptide | Period of time after administration | | |
|---|---|---|---|
| | 1 hr. | 3 hrs. | 6 hrs. |
| Peptide-1 | 2.63 ± 0.19 | 2.30 ± 0.13 | 1.71 ± 0.18 |
| Peptide-3 | 2.09 ± 0.18 | 2.46 ± 0.29 | 2.78 ± 0.15 |

EXAMPLE 19

Imaging of Inflammation Sites Using Technetium-99m Labeled Peptide

After Ravonal anesthesia was applied to the model rats described in EXAMPLE 18, 37–74 MBq of technetium-99m labeled Peptide-2 obtained in EXAMPLE 15, Peptide-4, Peptide-5, Peptide-6 and Peptide-7 obtained in EXAMPLE 17 were each administered to the respective tail vein. Images were obtained with gamma camera 30 minutes and one, three, and six hours later respectively. A site of interest was set on the image and the [T]/[B] ratio was determined. The [T]/[B] ratio, one hour after the administration, was 3.35 for Peptide-2, 4.98 for Peptide-6, 3.36 for Peptide-7, 4.27 for Peptide-4 and 4.41 for Peptide-5 whereby the focal site was evidently imaged. Table 2 shows time course of the [T]/[B] ratios (mean value±standard error) for three rats with respective peptides.

TABLE 2

[T]/[B] ratio of Tc-99m labeled peptide in inflammatory model rats

| Labeled Peptide | Period of time after administration | | | |
|---|---|---|---|---|
| | 30 mins | 1 hr. | 3 hrs. | 6 hrs. |
| Peptide-2 | — | 3.35 ± 0.33 | 2.78 ± 0.23 | 2.82 ± 0.17 |
| Peptide-4 | 2.47 ± 0.17 | 4.27 ± 0.26 | 3.10 ± 0.20 | — |
| Peptide-5 | 2.61 ± 0.08 | 4.41 ± 0.62 | 3.85 ± 0.63 | — |
| Peptide-6 | — | 4.98 ± 0.23 | 4.61 ± 0.49 | 3.20 ± 0.39 |
| Peptide-7 | — | 3.36 ± 0.31 | 2.18 ± 0.39 | 2.26 ± 0.20 |

EXAMPLE 20

Imaging of Rat Model with Infectious Disease Using Technetium-99m Labeled Peptide In 1.0 mL of physiological saline, $10^8$ of viable microbe cells of Staphylococcus aureus were suspended. An aliquot of 100 μl was administered intramuscularly to the right femoral region of Sparague-Davely Rats weighing about 220 g. After 24 hours, Ravonal anesthesia was applied to the model rats that had clearly evident inflammation; then, 37–74 MBq of technetium-99m labeled Peptide-6 obtained in EXAMPLE 8 was administered to the tail vein. Images were obtained with gamma camera one, three, and six hours later respectively. A site of interest was set on the image, and the [T]/[B] ratio was determined. One hour after the administration, the [T]/[B] ratio showed 1.92 indicating that focal region was evidently imaged. Table 3 shows time course of the [T]/[B] ratios (mean value±standard error) with this peptide.

TABLE 3

[T]/[B] ratio of Tc-99m labeled peptide in model rats with infectious disease

| Labeled Peptide | Period of time after administration | | |
|---|---|---|---|
| | 1 hr. | 3 hrs. | 6 hrs. |
| Peptide-6 | 1.92 ± 0.10 | 1.58 ± 0.05 | 1.52 ± 0.17 |

EXAMPLE 21

Safely of the Peptides

Assuming that clinical dosage to human is 1.0 mg/60 kg, bolus administration of Peptide-1, Peptide 4 and Peptide-5 in an amount of 8.3 μg per 1.0 g of rat and physiological saline as control were made respectively to the tail vein of the rat. Immediately after the administration, behavior of the rat was observed. The observation was continued until five days later; zero minute, ten minutes, three hours, six hours, one day, two days, three days, four days, and five days later. Just after the peptide administration, symptoms such as slobber, vomiting, ocular proptosis, and behavioral abnormality were not observed. Furthermore, extreme change in weight, i.e., weight gain or loss was not observed until five days later. After weighing five days later, the rats were dissected. Abnormality in tissue was checked with the naked eye; abnormality in any tissue was not noted such as hemostatis, pigmentation, or discoloration. These gave estimation that more than 1,000 times administration of the assumed clinical dosage would be safe.

As explained, the present invention provides a peptide and its chemically modified substances, radioactive metal labeled peptides derived therefrom, and radioactive diagnostics comprising such peptide, which are useful for imaging inflammation sites in living body of mammals including human and easy in preparation handling, and accumulate at inflammation sites immediately after the administration and stay there for a time suitable for imaging while being excellent in clearance via kidney into urine; thereby eliminating unnecessary exposure to patients, limitation of facilities for preparation, difficulty to get image information quickly, complicated handling and skill in preparation, and risk of infection to the operator. According to the present invention, the imaging is possible in several ten minutes after administration.

---

I claim:

1. A peptide having affinity for inflammatory cells and sites of inflammation, which consists of at least one of the following amino acid sequences:
LLGGPS (SEQ ID NO:1),
LLGGPSV (SEQ ID NO:2),
KEYKAKVSNKALPAPIEKTISK (SEQ ID NO:3),
KEYKCKVSNKALPAPIEKTISK (SEQ ID NO:4),
KTKPREQQYNSTYR (SEQ ID NO:5), and
KTKPREQQYNSTYRVV (SEQ ID NO:6),
wherein A, C, E, G, I, K, L, N, P, Q, R, S, T, V, and Y represent amino acid residues expressed by standard one-letter symbols.

2. A peptide construct having affinity for inflammatory cells and sites of inflammation, which comprises the peptide of claim 1 combined with a bifunctional cross linking agent.

3. A peptide complex having affinity for inflammatory cells and sites of inflammation, which comprises the peptide of claim 1 combined with a bifunctional ligand.

4. A peptide construct having affinity for inflammatory cells and sites of inflammation, which comprises the peptide of claim 2 combined with a carrier through the bifunctional cross linking agent.

5. A peptide construct having affinity for inflammatory cells and sites of inflammation according to claim 4, in which a bifunctional ligand is combined with the carrier.

6. A peptide construct having affinity for inflammatory cells and sites of inflammation according to claim 2, wherein the bifunctional cross linking agent is one selected from the group consisting of sulfosuccinimidyl 4-(N-maleimidemethyl)cyclohexane-1-carboxylate, 3-maleimidebenzoic acid N-hydroxysuccinimide ester, N-(ε-maleimidecaproyloxy) succinimide, and succinimydyl 4-(p-maleimidephenyl) butylate.

7. A peptide complex having affinity for inflammatory cells and sites of inflammation according to claim 3, wherein the bifunctional ligand is one selected from the group consisting of diethylenetriamine pentaacetic acid, ethylenediaminetetraacetic acid, and 1,4,7,10-tetraazacyclododecane-1-aminoethylcarbamoylmethyl-4,7,10-tris ((R,S)-methylacetic acid).

8. A peptide construct having affinity for inflammatory cells and sites of inflammation according to claim 4, wherein the carrier is polylysine or chitosan.

9. A peptide labeled with a radioactive metal, which comprises the peptide of claim 1, with which a radioactive metal ion is coordinated.

10. A peptide labeled with a radioactive metal according to claim 9, wherein the radioactive metal ion is technetium-99m or indium-111.

11. A radioactive diagnostic comprising the radioactive metal labeled peptide of claim 9.

12. A peptide construct having affinity for inflammatory cells and sites of inflammation according to claim 4, wherein the bifunctional cross linking agent is one selected from the group consisting of sulfosuccinimidyl 4-(N-maleimidemethyl)cyclohexane-1-carboxylate, 3-maleimidebenzoic acid N-hydroxysuccinimide ester, N-(ε-maleimidecaproyloxy) succinimide, and succinimydyl 4-(p-maleimidephenyl) butylate.

13. A peptide construct having affinity for inflammatory cells and sites of inflammation according to claim 5, wherein the bifunctional cross linking agent is one selected from the group consisting of sulfosuccinimidyl 4-(N-maleimidemethyl)cyclohexane-1-carboxylate, 3-maleimidebenzoic acid N-hydroxysuccinimide ester, N-(ε-maleimidecaproyloxy) succinimide, and succinimydyl 4-(p-maleimidephenyl) butylate.

14. A peptide complex having affinity for inflammatory cells and sites of inflammation according to claim 5, wherein the bifunctional ligand is one selected from the group consisting of diethylenetriamine pentaacetic acid, ethylenediaminetetraacetic acid, and 1,4,7,10-tetraazacyclododecane-1-aminoethylcarbamoylmethyl-4,7,10-tris ((R,S)-methylacetic acid).

15. A peptide construct having affinity for inflammatory cells and sites of inflammation according to claim 5, wherein the carrier is polylysine or chitosan.

16. A peptide complex labeled with a radioactive metal, which comprises the peptide complex of claim 3, with which a radioactive metal ion is coordinated.

17. A peptide construct labeled with a radioactive metal, which comprises the peptide construct of claim 5, with which a radioactive metal ion is coordinated.

18. A peptide complex labeled with a radioactive metal, which comprises the peptide complex of claim 7, with which a radioactive metal ion is coordinated.

19. A radioactive diagnostic comprising the radioactive metal labeled peptide of claim 10.

* * * * *